United States Patent
Mielnik et al.

(10) Patent No.: US 7,354,551 B2
(45) Date of Patent: Apr. 8, 2008

(54) ROOM DECONTAMINATION WITH HYDROGEN PEROXIDE VAPOR

(75) Inventors: Thaddeus J. Mielnik, Concord, OH (US); Eric W. Krieger, Mentor, OH (US); Donald L. Eddington, Winston-Salem, NC (US); George C. Koos, Concord, OH (US)

(73) Assignee: Steris Inc, Temecula, CA (US)

( * ) Notice: Subject to any disclaimer, the term of this patent is extended or adjusted under 35 U.S.C. 154(b) by 598 days.

(21) Appl. No.: 10/886,777

(22) Filed: Jul. 8, 2004

(65) Prior Publication Data

US 2006/0008379 A1    Jan. 12, 2006

(51) Int. Cl.
  *A61L 9/00* (2006.01)
(52) U.S. Cl. ...................................... 422/32
(58) Field of Classification Search ............... 422/28, 422/30, 32, 33, 300, 292
  See application file for complete search history.

(56) References Cited

U.S. PATENT DOCUMENTS 7,014,813 B1 *  3/2006 Watling et al. ............... 422/26

2002/0114727 A1 *  8/2002 McVey et al. .................. 422/4
2005/0074359 A1 *  4/2005 Krieger et al. ................ 422/28

FOREIGN PATENT DOCUMENTS

| EP | 0774263 A1 * | 5/1997 |
| WO | WO 01/21223 A1 * | 3/2001 |
| WO | WO 03/082355 A1 * | 10/2003 |

* cited by examiner

*Primary Examiner*—Walter D. Griffin
*Assistant Examiner*—Shanta G Doe
(74) *Attorney, Agent, or Firm*—Fay Sharpe LLP

(57) ABSTRACT

A system for microbially and/or chemically decontaminating a room such as a hotel room includes a vapor generator which supplies a decontaminant vapor, such as hydrogen peroxide vapor to the room. The room is then aerated to a level at which it is safe for normal occupants to enter. By using a two step aeration, with a second step at lower humidity than the first, the concentration of residual hydrogen peroxide is reduced rapidly to safe levels of 1 ppm or less, typically about 0.5 ppm, in under four hours. The room is rendered substantially free of contaminants, such as those responsible for Severe Acute Respiratory Syndrome (SARS), Norwalk virus, and unpleasant odors.

25 Claims, 2 Drawing Sheets

ROOM DECONTAMINATION WITH HYDROGEN PEROXIDE VAPOR

BACKGROUND OF THE INVENTION

The present invention relates to a method for decontamination of an enclosure, such as a hotel room, hospital ward, or laboratory. It finds particular application in the decontamination rooms containing soft furnishings and carpets, and will be described with particular reference thereto.

Large enclosures, such as rooms and buildings tend to become contaminated with a wide variety of microbial contaminants, including bacteria, molds, fungi, yeasts, and the like. These microorganisms thrive in damp spaces, such as behind walls, in plaster, under counters in bathrooooms, and tend to be very difficult to eradicate. For example fungi are allergenic agents and are occasionally infectious in susceptible people. They pose problems in buildings where moisture control is poor or water intrusion is common. Fungi grow in moist environments and form dormant, resistant spores, which are disseminated in the air. These spores tend to contact surfaces favorable for spore germination and outgrowth. Some contaminants are brought into the room in the air, both through doorways, windows and the like as well as through ventilation systems. Contaminants are also carried into the room on the clothing or person by people using the room and from breathing, particularly when the room is one which is used for bathing or sleeping, such as a hotel room. Microorganisms are often left in the room when the person leaves. These microorganisms are often able to survive in carpets, drapes, wallpaper, furniture, on countertops, and the like. Some microbes cause a musty smell. Others can infect later users of the room. Additionally, there is a possibility that a room may be intentionally contaminated with pathogenic microorganisms, such as anthrax spores, smallpox virus, or the like. Some contaminants, such as tobacco smoke, body perfume, and medicinal odors are non-microbial.

In the case of hotel rooms, hospital wards, and the like, where the occupancy of a room is changing frequently, it is desirable to ensure that microorganisms and other decontaminants left behind by one occupant do not lead to contamination of a subsequent occupant. Hotel rooms, with time and use, develop odors.

Microbial decontamination of rooms and buildings has been achieved in the past using formaldehyde. However, formaldehyde is highly carcinogenic and powder residues must be recovered after the microbial decontamination process. Recovery of toxic gases from dilution air, leaking air, and the degassing of gas absorptive materials in the decontaminated room or building is difficult and time consuming. Further, care must be taken and monitors placed to ensure that the toxic gas does not escape into the surrounding areas.

Hydrogen peroxide vapor has been used for atmospheric pressure microbial decontamination of enclosures, isolated environments and their contents, and also such under vacuum conditions as a sterilizer of medical devices, and the like. Hydrogen peroxide vapor is a particularly useful sterilant for these purposes because it is effective at low temperatures. Vaporized hydrogen peroxide systems provide dry, rapid, low-temperature decontamination of sterilizer contents that are contaminated with microorganisms, including spore-forming bacteria. Keeping the temperature of the sterilizer near room temperature eliminates the potential for thermal degradation of associated equipment and items to be sterilized. In addition, hydrogen peroxide readily decomposes to water vapor and oxygen, which, of course, are not harmful to the humans including technicians and people nearby.

Typically, a slightly negative or positive pressure is used in the sterilizer. A solution of about 35% hydrogen peroxide in water is injected into a vaporizer as fine droplets or mist through injection nozzles. The droplets fall on a flat heated surface which heats the droplets to form the vapor, without breaking it down to water vapor and oxygen. A carrier gas is circulated over the heat transfer surface to absorb the peroxide vapor.

For optimally effective sterilization, the hydrogen peroxide is maintained in the vapor state. Sterilization efficiency and material compatibility are reduced by condensation. In the case of larger enclosures, difficulties arise in maintaining the conditions throughout the enclosure such that the hydrogen peroxide remains in the vapor state.

Hotel rooms are often cleaned with a bleach solution. However, bleach often leaves a chlorine odor. Plus, bleach is not color-safe on many fabrics, wall coverings, and carpets. Drapes are typically dry cleaned, an expensive and time consuming process. Shampooing rugs can leave them so damp that the room cannot be rented for a night—a significant revenue loss. Dry powder disinfectants applied to carpets leave the room with an odor of their own and tend to have a short-lived effect.

The present invention provides a new and improved system and method of decontaminating an enclosure which overcome the above-referenced problems and others.

SUMMARY OF THE INVENTION

In accordance with one aspect of the present invention, a method for decontamination of an enclosure and items within the enclosure and for rendering the enclosure safe for human occupancy is provided. The method includes decontaminating the enclosure and items within the enclosure including introducing a decontaminant in the form of a vapor to the enclosure, and maintaining the decontaminant within the enclosure for a sufficient time to decontaminate the enclosure and items within the enclosure. After the decontaminating step, decontaminant is removed from the enclosure to a level at which it is safe for the enclosure to be occupied by a person.

In accordance with another aspect of the present invention, a method for decontamination of a room which includes at least one of a carpet and soft furnishings is provided. The method includes introducing hydrogen peroxide in the form of a vapor to the enclosure and after a period of time sufficient to decontaminate the room, aerating the room to remove residual hydrogen peroxide. The aeration step includes aerating the room for a first period of time and lowering a humidity level in the room.

In accordance with another aspect of the present invention, a method for periodically refreshing a hotel room to remove stale odor is provided. The method includes introducing hydrogen peroxide vapor to the room and maintaining hydrogen peroxide vapor in the room for a period of time sufficient to reduce the stale odor. The method further includes removing residual hydrogen peroxide from the room until a hydrogen peroxide concentration in the room reaches a first level, reducing the humidity level in the room, and removing hydrogen peroxide from the room until the hydrogen peroxide concentration reaches a second level lower than the first level, such that the hotel room is decontaminated in under about four hours.

One advantage of at least one embodiment of the present invention is that it ensures that a room is free of harmful pathogenic microorganisms or chemical agents.

Another advantage of at least one embodiment of the present invention is that it freshens rooms removing or reducing unpleasant odors.

Another advantage of at least one embodiment the present invention is that it enables decontamination of a room within a short period of time.

Another advantage of at least one embodiment the present invention is that residual amounts of decontaminant are minimized and are not harmful.

Another advantage of at least one embodiment the present invention is that residual amounts of microbial decontaminant rapidly degrade to water vapor and oxygen.

Another advantage of at least one embodiment the present invention is that it enables rooms fitted with carpets, drapes and other soft furnishings, wallpaper, and electronic equipment to be decontaminated.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
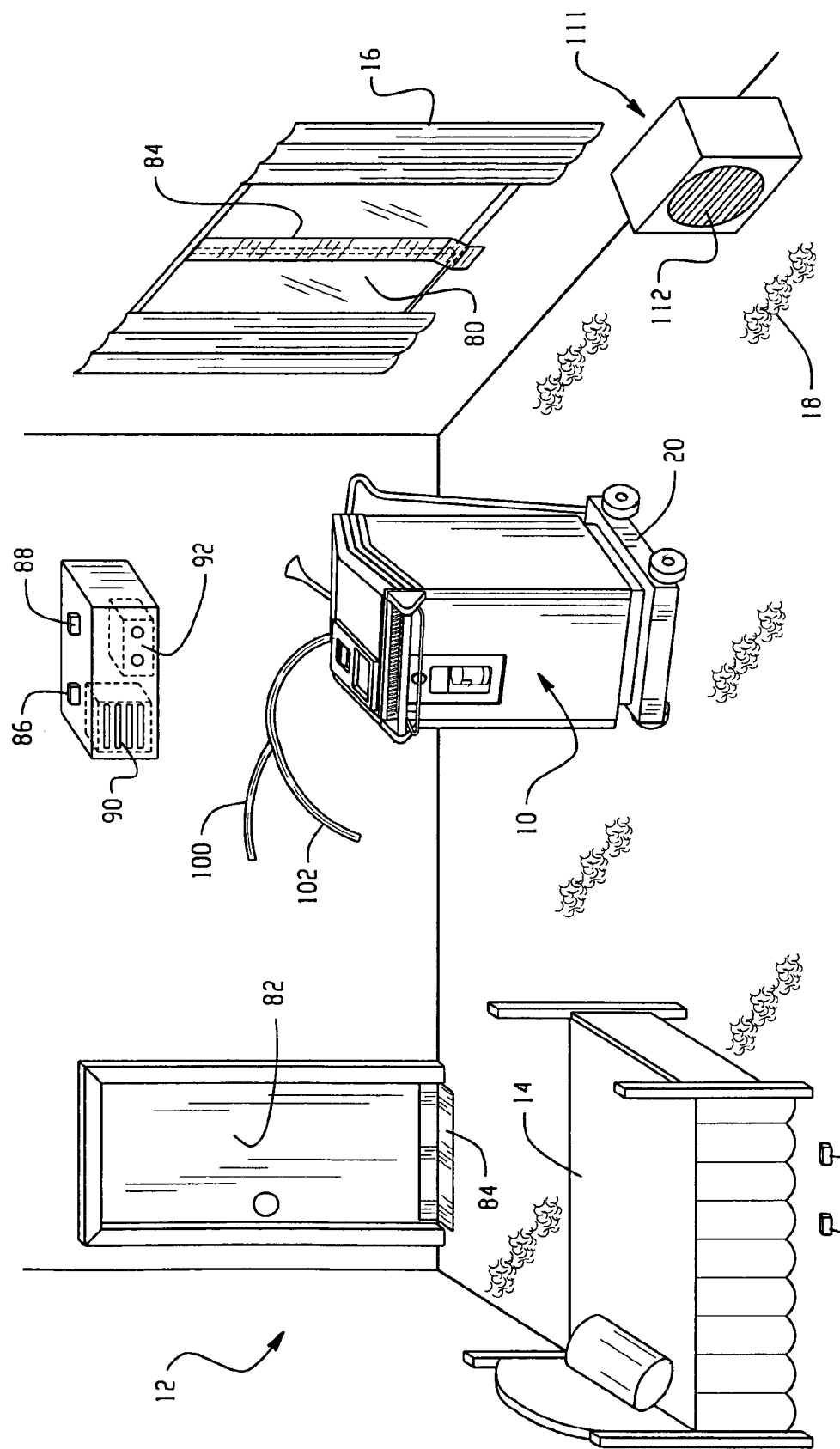
FIG. 1 is a perspective view of a hotel room containing a mobile hydrogen peroxide vapor generator and free-standing blower unit for microbial and chemical decontamination of the room according to the present invention.

With reference to FIG. 1, a room decontamination system includes a source 10 of a decontaminant gas, such as a hydrogen peroxide generation system. The system is used to supply the vapor to an enclosure 12, such as a room. Thus, the enclosure will generally have an interior volume of at least 25 $m^3$ and more typically, at least about 80 $m^3$, or higher. In the illustrated embodiment, the enclosure 12 is a hotel room or suite, containing a bed 14 and other soft furnishings, such as window drapes 16. A carpet 18 covers at least a part of the floor of the room. Wallpaper, which may be printed in various colors, covers the walls. A bathroom (not shown) is connected with the room(s). It will be appreciated that while particular reference is made to the decontamination of hotel rooms, the decontamination system has application in other enclosures which are capable of being substantially isolated from the surrounding environment, including hospital wards, laboratories, airport lounges, cruise ship cabins, meeting rooms, waiting rooms, dining facilities, and the like, all of which are considered herein to be rooms.

The generation system 10 is mounted on a wheeled cart 20, or is otherwise mobile, so that it is readily transported into and out of the room 12.

The decontaminant gas is one which is capable of destroying or reducing the concentration of at least one microorganism or pathogenic chemical agent within the room 12, present in the air and/or on furnishings, carpeting, counter tops, furniture and the like.

Different levels of decontamination are contemplated. As used herein, the term "decontamination," and its equivalents, is intended to encompass both microbial decontamination as well as chemical decontamination—the destruction of chemical agents, or their conversion to harmless or odorless compounds. Decontamination also encompasses the neutralizing of unpleasant odors, such as tobacco smoke, perfume, or body odor residues, and odors and dampness due to molds. "Microbial decontamination" is used herein to encompass the destruction of biological contaminants, specifically, living microorganisms, and also the destruction or inactivation of pathogenic forms of proteinaceous-infectious agents (prions). The term microbial decontamination encompasses sterilization, the highest level of biological contamination control, which connotes the destruction of all living microorganisms. The term also includes disinfection, the destruction of harmful microorganisms, and sanitizing, which connotes being free from germs. "Chemical decontamination" is intended to encompass the destruction of pathogenic chemical agents or their conversion to less harmful or odiferous species.

Exemplary biological contaminants which are destroyed in the decontamination process include bacterial spores, vegetative bacteria, viruses, molds, and fungi. Some of these are capable of killing or causing severe injury to mammals, particularly humans. Included among these are viruses, such as equine encephalomyelitis and smallpox, the coronavirus responsible for Severe Acute Respiratory Syndrome (SARS); bacteria, such as those which cause plague (*Yersina pestis*), anthrax (*Bacillus anthracis*), Norwalk virus, and tularemia (*Francisella tularensis*); and fungi, such as coccidioidomycosis; as well as toxic products expressed by such microorganisms; for example, the botulism toxin expressed by the common *Clostridium botulinium* bacterium.

Also included are the less harmful microorganisms, such as those responsible for the common cold (rhinoviruses), influenza (orthomyxoviruses), skin abscesses, toxic shock syndrome (*Staphylococcus aureus*), bacterial pneumonia (*Streptococcus pneumoniae*), stomach upsets (*Escherichia coli, Salmonella*), and the like.

Exemplary pathogenic chemical agents include substances which are often referred to as chemical warfare agents, such as poison gases and liquids, particularly those which are volatile, such as nerve gases, blistering agents (also known as vesicants), and other extremely harmful or toxic chemicals. As used herein, the term "chemical pathogenic agent" is intended to include only those agents which are effective in relatively small dosages to substantially disable or kill mammals and which can be degraded or otherwise rendered harmless by a process which includes oxidation.

Exemplary chemical pathogenic agents include choking agents, such as phosgene; blood agents, which act on the enzyme cytochrome oxidase, such as cyanogen chloride and hydrogen cyanide; incapacitating agents, such as 3-quinuclidinyl benzilate ("BZ"), which blocks the action of acetylcholine; vesicants, such as di(2-chloroethyl)sulfide (mustard gas or "HD") and dichloro(2-chlorovinyl)arsine (Lewisite); nerve agents, such as ethyl-N, N dimethyl phosphoramino cyanidate (Tabun or agent GA), o-ethyl-S-(2-diisopropyl aminoethyl) methyl phosphono-thiolate (agent VX), isopropyl methyl phosphonofluoridate (Sarin or Agent GB), methylphosphonofluoridic acid 1,2,2-trimethylpropyl ester (Soman or Agent GD).

Hydrogen peroxide vapor is a particularly effective microbial and chemical decontaminant because it has broad spectrum activity against a wide variety of pathogenic microorganisms and chemical pathogenic agents, such as hard to destroy spores of *Bacillus stearothennophilus, Bacillus anthracis*, smallpox virus, and the like. It is also effective at or close to room temperature (e.g., 15-30° C.), making it suitable for decontamination of enclosures with little or no heating. Hydrogen peroxide vapor has a good material compatibility, rendering it safe for use with a variety of equipment and materials, including electronic equipment, such as television sets, radios, and the like, carpets, wallpaper, fabric covered and wood furniture, brass and chrome fixtures, and the like. It also degrades to water and oxygen over time, which are not harmful to people subsequently entering the treated space. Where low levels of hydrogen peroxide (about 1 ppm, or less) remain in the room after decontamination, this is not considered to pose a risk to the occupants.

A suitable hydrogen peroxide generation system 10 is a VHP® 1000 vapor generator, available from STERIS Corp, Mentor, Ohio. Such systems are capable of sterilizing enclosures 12 of up to about 210 m$^3$. For larger enclosures, multiple mobile hydrogen peroxide vapor generators 10 are used. While hydrogen peroxide vapor is a preferred microbial decontaminant, it is also contemplated that other gaseous microbial decontaminants are used, alone or in combination with hydrogen peroxide vapor, such as other peroxy compounds and peracids, e.g., peracetic acid. Preferably, the microbial decontaminant is one which readily decomposes to products which are not harmful to subsequent occupants of the room, maintenance staff, and the like and which do not have a strong or long lasting unpleasant odor.

To deactivate contaminants in air and on surfaces throughout the room 12, it has been found that a concentration of hydrogen peroxide of about 0.1-2 mg/L, or more, at about 25° C. is effective to decontaminate the room in about 30 minutes or less. Longer times may be used at lower concentrations or for large enclosures, or shorter times at higher concentrations. The vapor is preferably in the "dry" state, i.e., below the saturation point of the vapor, which varies with temperature. This avoids droplets of the vapor condensing on items in the room, which both reduces the effectiveness of the vapor and increases the time needed to remove the residual hydrogen peroxide after the vapor decontamination cycle is complete. Keeping the vapor in the dry state also reduces the risk of damage to electronic components, running of colors in fabrics and wallpapers, and other items susceptible to water damage.

Figure 2:
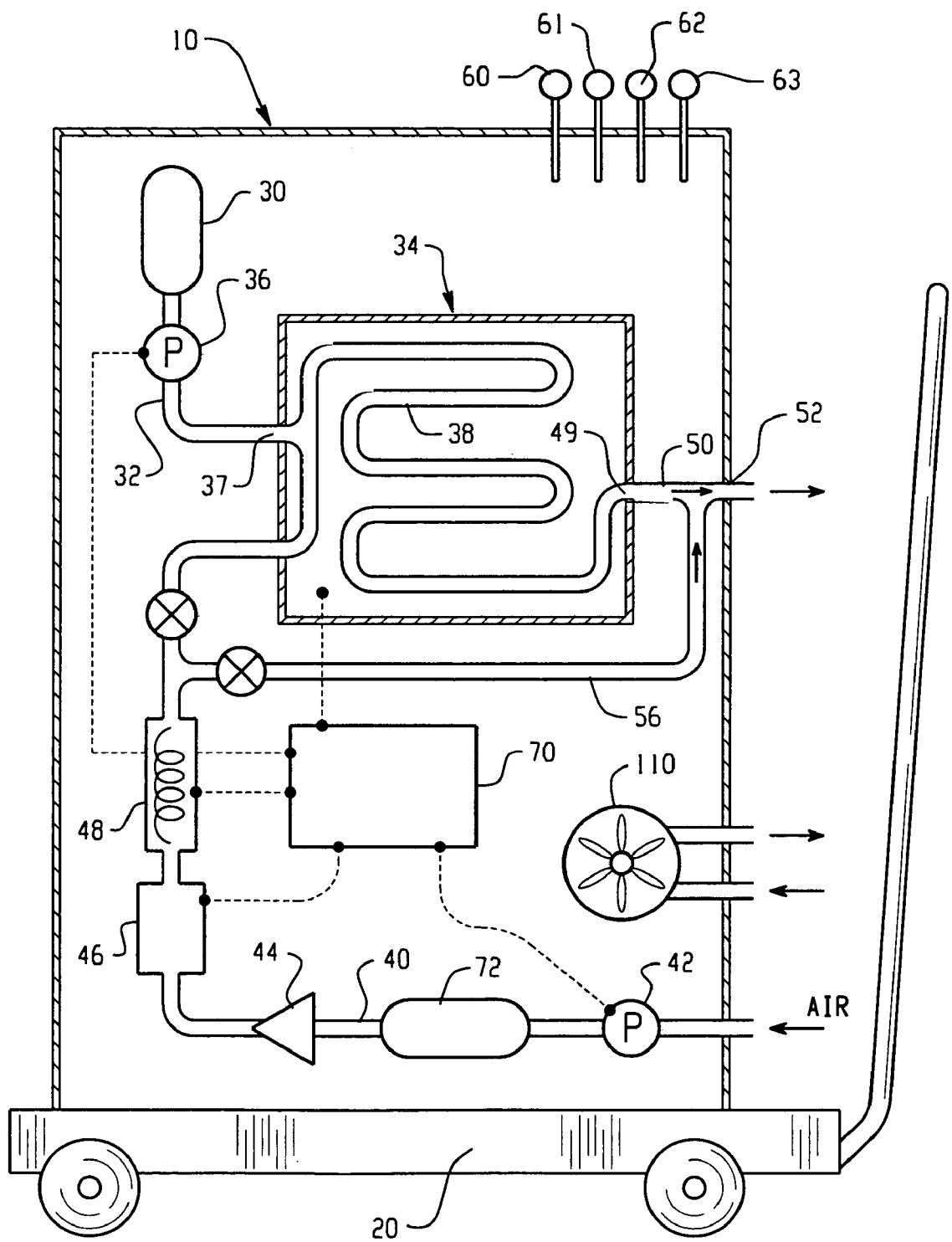
FIG. 2 is a schematic side view of the mobile hydrogen peroxide vapor generator of FIG. 1.

With reference to FIG. 2, the hydrogen peroxide vapor is readily formed from a solution of hydrogen peroxide in water, such as a 35% hydrogen peroxide solution, which is supplied from a reservoir 30, such as a tank, via a fluid delivery line 32 to a vaporizer 34. A delivery means, such as a pump 36, gravity feed, or the like is optionally employed to deliver the solution at a selected rate to an inlet 37 of the vaporizer. The vaporizer 34 converts the liquid to a vapor, for example, by bringing droplets or a mist of the solution into contact with a heated plate or tube 38. Other gaseous oxidizing agents may be used, such as peracids, e.g., peracetic acid vapor, ozone, or alcohol, alone, or in combination with one or more gaseous oxidants including hydrogen peroxide vapor.

The hydrogen peroxide concentration in the solution is selected according to the desired vapor concentration. For example, the hydrogen peroxide concentration may be from 25-65% by weight hydrogen peroxide in aqueous solution. In one embodiment, the hydrogen peroxide concentration is from about 30-40% by weight aqueous hydrogen peroxide. At this level, condensation of hydrogen peroxide is limited, while microbial decontamination is achieved in a short period of time.

A carrier gas, such as air, is supplied to the vaporizer 34 via a carrier gas line 40 to mix with the liquid and/or vapor and carry the vapor out of the vaporizer 34. As illustrated in FIG. 2, a pump 42, such as a compressor, pressurizes air from the room and feeds it to the carrier gas line 40. Alternatively, the carrier gas is optionally supplied from a source (not shown) such as a pressurized gas cylinder. The carrier gas may be filtered by a filter 44, dehumidified by a dehumidifier 46, such as a desiccant material, and optionally heated by a heater 48 before entering the vaporizer 34. The carrier gas is fed into the tube 38, or is otherwise mixed with the hydrogen peroxide solution and/or the forming vapor in the vaporizer. The vapor and carrier gas mixture passes from the vaporizer outlet 49 into a duct 50 which is connected with an outlet 52 of the system 10.

Optionally, all or a portion of the carrier gas bypasses the vaporizer via a bypass line 56 which connects the carrier gas line 40 with the duct. The bypassing carrier gas mixes with the remaining carrier gas (which has passed through the vaporizer) and vapor in the duct 50.

Sensors 60, 61, 62 such as hydrogen peroxide sensors 60, water vapor sensors 61, a dew point temperature measuring device 62, and/or detectors 63 for selected anticipated chemical or biological contaminants, are optionally associated with the vapor generation system 10 or separately positioned throughout the room 12 prior to decontamination.

The "room," as used herein, includes the entire interior volume including attached bathrooms, closets, sitting or sleeping alcoves, and the like.

The various components of the vaporization system 10, such as pumps 36, 42, heaters 48 vaporizer 34, and the like, are controlled by a central control system 70. Sensors 60, 61, 62 and detectors 63 are optionally also linked to the control system 70, providing feedback of detected concentrations of hydrogen peroxide, water vapor, and optionally chemical and or biological contaminant levels in the room. In this way, the system components can be adjusted to maintain a hydrogen peroxide concentration within the room within a preselected range, such as from about 0.1-5 mg/L (72-3600 ppm), e.g., from 0.1-2.0 mg/L. In one embodiment, the hydrogen peroxide concentration is at least about 0.7 mg/L (400+ppm). For example, the control system 70 adjusts the rate of introduction of hydrogen peroxide to the vaporizer, air flow rates, or the like, in response to detected hydrogen peroxide/water concentrations, to maintain the selected hydrogen peroxide concentration in the room 12. Suitable hydrogen peroxide sensors 60 are those which use infrared absorption by the vapor circulating in the room 12. The sensor preferably operates in a region of the infrared spectrum where water and/or hydrogen peroxide absorbs strongly, to provide a measure of the hydrogen peroxide concentration. Alternatively, an electrochemical hydrogen peroxide detector is employed.

In one embodiment, a recirculating system is employed. In this embodiment, spent vapor from the room is returned to the vapor generation system 10. The spent vapor optionally passes through a catalytic converter 72 to convert residual hydrogen peroxide to water vapor and oxygen prior to reaching the vaporizer 34. As shown in FIG. 2, the returning vapor is passed through the dehumidifier 46 and heater 48 in air inlet line 40 before reentering the vaporizer. The line 40 is also employed for lowering the humidity of the room to a preselected relative humidity level, prior to admitting hydrogen peroxide. This reduces the likelihood of condensation of vapor on walls, carpeting, furnishings, and the like, which tends to reduce the effectiveness of the microbial decontaminant.

An exemplary room decontamination process takes place as follows. Operators familiar with the vapor generation system 10 wheel the system into a room 12 which is to be refreshed or which is known to be or suspected of being contaminated with a microorganism or chemical agent. The operators may don protective clothing and respirators prior to entering the room if the risk posed by the contaminant is perceived to be significant. It is also contemplated that the decontamination process be carried out periodically, simply as a precautionary measure or for removing non harmful, but unpleasant odors within the room.

Windows 80, doors 82, and other points of potential air leakage are optionally sealed with tape 84 or the like (FIG. 1). Optionally, one or more sensors 86 and/or detectors 88, similar to sensors and detectors 60, 61, 62, 63 are positioned in various locations around the room 12. These are evaluated following the decontamination process to ensure that all areas of the room received adequate supplies of the decontaminant to ensure the desired level of decontamination.

Where the room 12 is fitted with a dehumidifier 90, such as a condenser-type dehumidifier which incorporates a cooling coil, the room's dehumidifier is optionally switched to a setting which reduces the humidity level of the room to a suitable level to begin decontamination. Alternatively or additionally, the dehumidifier 46 and compressor 42 of the decontamination system 10 are operated to lower the humidity level of the room to the preselected level. Where the room is fitted with a heating system 92, this is optionally switched to heat the room to a suitable level for decontamination, e.g., ambient temperatures of about 20-30° C. By maintaining the room at a relatively constant temperature throughout decontamination, the likelihood of vapor condensation is reduced. The room dehumidification and heating system(s) 90, 92 (which may be combined into a single room heating and air conditioning unit as a fixture of the room) is preferably isolated from any centralized heating and/or cooling system, such as a HVAC system, of the facility in which the room is located. This is to avoid transfer of the decontaminant gas to other rooms in the facility. If the system 90, 92 is not readily isolated, it is switched off. However, the room air conditioner may have ducts which circulate conditioned air to the bathroom, sitting and sleeping areas, and the like.

At some point prior to decontamination, the operators exit the room 12. Optionally, the control system 70 may be linked by suitable electrical cables (not shown) or by telemetry to a separate control system positioned outside the room which allows the operator to control the decontamination process. Alternatively, the decontamination process is under the automated control of the control system 70.

Once the humidity level in the room 12 is at a preselected level (which may be detected by the water vapor sensor 61), the decontamination phase commences. The room dehumidifier 90 is switched off, although its fan may continue to operate to circulate the decontaminant gas through the duct work and to remote areas. Carrier gas and decontaminant solution are fed to the vaporizer 34, vaporized, and delivered as a vapor mixture to the outlet 52 of the system. The outlet 52 of the vapor generation system 10 is optionally connected to two or more fluid lines 100, 102 (FIG. 1), such as flexible hoses, to deliver the vapor to locations spaced around the room 12. Or, the vapor may be simply emitted from the single outlet 52. In yet another embodiment, one or more fluid lines is connected with a blower (not shown) of the room dehumidification and heating system 90, 92, to assist in distributing the vapor throughout the room. However, dehumidification or heating of the vapor by the room system is to be avoided as this can lead to destruction of the hydrogen peroxide, and/or concentrating hydrogen peroxide to a level at which a spontaneous explosion of the hydrogen peroxide may occur.

The hydrogen peroxide is fed to the room 12 for a sufficient period of time to ensure that the desired level of decontamination is achieved throughout the room. The control system 70 optionally controls the vaporizer, pumps, and other components of the generation system in response to detected levels of hydrogen peroxide, water vapor, and/or sensed contaminants in the room to ensure the desired vapor concentration and or decontamination level is achieved. Optionally, the control system 70 additionally or alternatively adjusts the decontamination period (shorter or longer time) in response to detected levels to ensure decontamination is achieved.

In yet another embodiment, the control system 70 is programmed to feed a specified amount of vapor over a preselected period of time into the room in accordance with input parameters, such as the size of the room, level of furnishings and carpeting, room temperature, and the like.

In yet another embodiment, the control system 70 is programmed to increase the hydrogen peroxide vapor and water vapor to a specific dew point temperature as measured by detector 62. The dew point temperature can be set using the control system based on the temperature of the room, such that the system will avoid producing condensation of liquid decontamination agents on room furnishings at levels which may be dangerous.

For a typical hotel room of about 50 $m^2$ in area, using a VHP® 1000 vapor generator, and a hydrogen peroxide concentration of about 0.1-2 mg/L, a room is decontaminated in about 30 minutes or less from the start of hydrogen peroxide generation. Optionally, the length of the decontamination process is under the control of the control system 70.

In one embodiment, the hydrogen peroxide vapor is maintained at a concentration in the room 12 until the decontamination is complete, and is continually replenished to maintain prescribed concentration levels. In another embodiment, the hydrogen peroxide is replaced periodically, or is allowed to decline naturally, once an optimum level has been achieved.

After the decontamination process is completed, the room is aerated to remove residual amounts of hydrogen peroxide. By "aeration" it is meant the introduction of air into the room at a hydrogen peroxide concentration which is lower than that of the room. Fresh air is fed to the room, for example, by the system 10. Specifically, air drawn in into the system by the compressor 42 is stripped of spent vapor by the catalytic converter and recirculated to the room via the outlet 52. Alternatively or additionally, a blower 110, which may be mounted on the cart 20, as illustrated in FIG. 2, is used to assist in recirculating the air around the room room.

Alternatively, a freestanding aeration unit 111, which comprises a blower 112, is positioned elsewhere in the room (FIG. 1). The unit 111 assists in circulating the aeration air around the room. A suitable blower 110, 112 is one which operates as about 20-25 m³/minute. In one embodiment, the aeration unit 111 includes one or more catalytic converters 113, such as two or more catalytic converters in series, which destroy hydrogen peroxide in the room air. The blower draws or passes the room air through the catalytic converters and out into the room. The aeration unit optionally also includes a dehumidifier 114 for removing moisture from the air. The dehumidifier 114 is preferably of the condensing-type, which incorporates a cooling coil. The condenser condenses both water vapor and hydrogen peroxide from the air. However, because the hydrogen peroxide is in only trace amounts at this stage, it does not reach a level in the condensate where it may pose a hazard. An aeration unit 111 with a 20-25 m³/minute blower of this type is effective at lowering the room hydrogen peroxide concentration from about 0.1-2.0 mg/L to about 3-5 ppm, as measured with a Draeger tube, in under three hours, when used for the second stage of the process (below about 20-30 ppm hydrogen peroxide).

The combined action of the catalytic converters and the condensing dehumidifier rapidly reduce the residual levels of hydrogen peroxide to below 1 ppm, typically, in under an hour from the time at which the dehumidifier 90, 114 is switched on. However, it is also contemplated that the catalytic converters may be switched off in this stage, allowing the dehumidifier(s) 90, 114 to remove the hydrogen peroxide simply by condensation.

In another embodiment, windows 80 of the room are optionally opened to allow fresh air into the room and vapor laden air out of the room to assist in aeration. In such instances, a blower similar to blower 112 is located in or adjacent the window opening.

The hydrogen peroxide concentration is reduced to a level at which it is considered completely safe for occupants to remain in the room for extended periods without respirator equipment. Preferably, the concentration of the hydrogen peroxide is reduced to 1 ppm, or less. More preferably, the hydrogen peroxide concentration is reduced to about 0.5 ppm, or less.

It has been found that carpeting, and to some extent, the soft furnishings present in the room, such as draperies, mattresses, chairs, and the like, tend to absorb hydrogen peroxide and release it slowly. Thus, while it is relatively easy to reduce hydrogen peroxide levels by the methods described to about 3-5 ppm, decreasing the hydrogen peroxide to about the 1 ppm level or below can take several days to complete, even using a sizable blower.

It has been found that by lowering the humidity level in the room for the last stages of hydrogen peroxide removal (including the stage of removal below about 3 ppm) a much more rapid removal of hydrogen peroxide is achieved. With this method, it is possible to lower the hydrogen peroxide to about 0.5 ppm in under four hours, generally in about 3 hours or less from the start of the aeration period. A two step aeration procedure is thus employed in which a first step is carried out at about a first humidity level and a second aeration step is carried out at a lower humidity level. A decontamination process, from the start of hydrogen peroxide delivery to allowing access to the room can thus readily be completed in four hours.

To achieve the lowered humidity for the final stage, the room's own dehumidification system 90 is preferably used. Alternatively, or additionally the dehumidifier 46 in the system 10 is used and/or a separate dehumidifier (not shown) is brought into the room to carry out the last stages of dehumidification. Where several rooms are to be decontaminated, it may be desirable to remove the system 10 from the room prior to aeration, or part way through the aeration, so that it can be moved to the next room to be treated.

At about the 3 ppm hydrogen peroxide level, the room 12 is generally quite safe for operators to spend short periods of time within the room, for example, for removing or checking sensors 60, 61, 62, 86 and detectors 63, 88, removing the mobile vapor generation system 10, or for switching on and/or changing settings on the room dehumidifier 90.

The low level of humidity used for removal of the last few ppm of hydrogen peroxide is preferably not used during the decontamination stage or during the early stages of hydrogen peroxide removal (e.g., above about 20-30 ppm hydrogen peroxide). Aerating the enclosure thus continues as described above until the decontaminant is at a concentration which is less than half of the concentration of the decontaminant during the decontaminating step. This is because the condensation of humidity from the air when there are still significant amounts of hydrogen peroxide present can lead to preferential condensation of hydrogen peroxide. It may also pose a risk of material damage, or ignition of non-compatible materials, which can occur when hydrogen peroxide reaches very high concentrations in liquid form.

For example, in the early stages of hydrogen peroxide removal, the relative humidity in the room can be about 30%, or above, e.g., at least 40%. For the last stages of removal, e.g., for hydrogen peroxide levels of 10 ppm. or below (particularly for levels of about 5 ppm and below, and most particularly for levels of 3 ppm and below), the relative humidity is preferably dropped to about 20% or below.

In one embodiment, the hydrogen peroxide concentration in a room, such as a hotel room, is reduced from a level of about 3-5 ppm hydrogen peroxide to about 0.5 ppm hydroxide by operating the room air conditioning and dehumidification system 90 in combination with a blower 112, as described above in under one hour, generally in about 45 minutes.

In addition to or in place of the second aeration step at low humidity, a chemical dryer, UV generator, conventional hot water carpet cleaning machine, or the like (not shown) is used to assist in removing or breaking down hydrogen peroxide from carpets, soft furnishings, and the like.

The operators optionally keep a periodic check on the various hydrogen peroxide sensors 60, 86 around the room to determine when the safe level has been achieved. Where multiple rooms of the same type are being decontaminated, this may not be necessary as the expected time to completion will be similar for each room. Once the level is verified to be at a safe level, e.g., at around 1 ppm, or less, the room is ready for reoccupation.

Rooms decontaminated in this way smell fresh and are free of unpleasant odors as well as having the assurance of being microbially and chemically decontaminated.

Without intending to limit the scope of the invention, the following example demonstrates the effectiveness of the decontamination system.

EXAMPLE

A STERIS VHP 1000™ hydrogen peroxide vapor generator is wheeled into a hotel room fitted with a bed and other standard room furnishings. Any air gaps in the room are sealed with tape. The vapor generator is operated to deliver hydrogen peroxide vapor into the room until a concentration of above 0.1 mg/L is achieved at a temperature of about 25° C. The hydrogen peroxide is maintained in the room for about thirty minutes. The vapor generator is then switched off. A freestanding blower with a capacity of 20-25 m³/minute is positioned in the room. The blower is equipped with a series of catalytic converters and is used to remove hydrogen peroxide and circulate the treated air around the room. The blower also includes a dehumidification system for removing moisture from the air. The windows of the room remain closed during aeration. The hydrogen peroxide concentration in the room is reduced from about 0.7 mg/L to about 3-5 ppm in under three hours, as measured with a Draeger tube. The room air conditioning system is then switched on full to reduce the humidity level in the room. The blower continues to break down and remove hydrogen peroxide for an additional 45 minutes at which time the hydrogen peroxide concentration is 0.5 ppm. Tests on the liquid condensed by the room dehumidifier show it to be primarily water, without high concentration levels of hydrogen peroxide.

A comparison test is carried out as described above, but without the use of the room air conditioning system. In this test, the hydrogen peroxide concentration is still at about 3-5 ppm after 12 hours of aeration.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method for decontamination of a room which includes at least one of a carpet and soft furnishings comprising:
   introducing hydrogen peroxide in the form of a vapor to the room, and
   after a period of time sufficient to decontaminate the room, removing residual hydrogen peroxide including the sequential steps of:
      removing hydrogen peroxide from the room to lower a hydrogen peroxide concentration in the room to a first concentration level; and
      after the hydrogen peroxide concentration has reached the first level, operating a condensing-type dehumidifier until the hydrogen peroxide concentration reaches a second level, lower than the first level.

2. The method of claim 1, wherein the step of removing hydrogen peroxide from the room includes destroying hydrogen peroxide with a catalytic converter.

3. The method of claim 1, wherein the hydrogen peroxide concentration in the room at the first concentration level is less than about 30 ppm.

4. The method of claim 3, wherein the hydrogen peroxide concentration in the room at the first concentration level is less than about 5 ppm.

5. The method of claim 2, wherein the hydrogen peroxide concentration at the second level is less than about 1 ppm.

6. The method of claim 1, wherein the step of operating a condensing-type dehumidifier further includes blowing air throughout the room.

7. The method of claim 1, wherein the step of operating a condensing-type dehumidifier further includes operating a catalytic converter to destroy hydrogen peroxide present in the room.

8. The method of claim 1, wherein the condensing-type dehumidifier forms a part of a mobile aeration unit.

9. The method of claim 8, wherein the mobile aeration unit further includes at least one of a blower and a catalytic converter.

10. The method of claim 1, wherein the condensing-type dehumidifier includes a room air conditioning system.

11. The method of claim 1, wherein the condensing dehumidifier is only operated while the concentration of hydrogen peroxide in the room is below 30 ppm.

12. The method of claim 1, wherein the room is a hotel room.

13. The method of claim 1, wherein the step of removing hydrogen peroxide to the first concentration level includes blowing air into the room at a hydrogen peroxide concentration which is lower than a hydrogen peroxide concentration in the room.

14. The method of claim 1, wherein the step of removing hydrogen peroxide is concluded in less than about four hours.

15. The method of claim 1, wherein the step of operating the condensing-type dehumidifier reduces the hydrogen peroxide concentration from about 5 ppm to less than 1 ppm in under one hour.

16. A method for decontamination of an enclosure and items within the enclosure and for rendering the enclosure safe for human occupancy comprising:
   decontaminating the enclosure and items within the enclosure including:
      introducing a decontaminant containing hydrogen peroxide and water in the form of a vapor to the enclosure, and
      maintaining the decontaminant vapor within the enclosure for a sufficient time to decontaminate the enclosure and items within the enclosure;
   after the decontaminating step, removing decontaminant from the enclosure to a level at which it is safe for the enclosure to be occupied by a person, including:
      condensing water vapor and hydrogen peroxide vapor from the room with a condenser only after the hydrogen peroxide vapor concentration in the room has dropped below about half of the concentration of the hydrogen peroxide vapor during the decontaminating step.

17. The method of claim 16, wherein the enclosure includes a room, the room having at least one of a carpet, draperies, fabric covered furniture, and wallpaper.

18. The method of claim 16, wherein the step of removing decontaminant is completed in under about four hours.

19. The method of claim 16, wherein the step of removing decontaminant includes:
   aerating the enclosure.

20. The method of claim 19, wherein the aeration step is continued until the decontaminant concentration vapor is less than 10 ppm.

21. The method of claim 16, wherein the step of condensing is continued until the hydrogen peroxide vapor is less than about 1 ppm.

22. The method of claim 21, wherein the hydrogen peroxide vapor is reduced to a level of to about 0.5 ppm.

23. The method of claim 16, wherein the step of removing decontaminant includes aerating the enclosure until the decontaminant is at or about a safe level for people to return to the room.

24. The method of claim 16, wherein the step of removing decontaminant includes:
   a first removal step which is carried out at a first humidity level; and a second removal step which is carried out at a second humidity level which is below the first humidity level.

25. A method for periodically refreshing a hotel room to remove a stale odor comprising:

introducing hydrogen peroxide vapor to the room;

maintaining hydrogen peroxide vapor in the room for a period of time sufficient to reduce the stale odor;

removing residual hydrogen peroxide from the room until a hydrogen peroxide concentration in the room reaches a first level;

only after the concentration in the room reaches the first level, reducing the humidity level in the room with a condenser;

removing hydrogen peroxide from the room until the hydrogen peroxide concentration reaches a second level lower than the first level, such that the hotel room is decontaminated in under about four hours.

* * * * *